Figure 1:
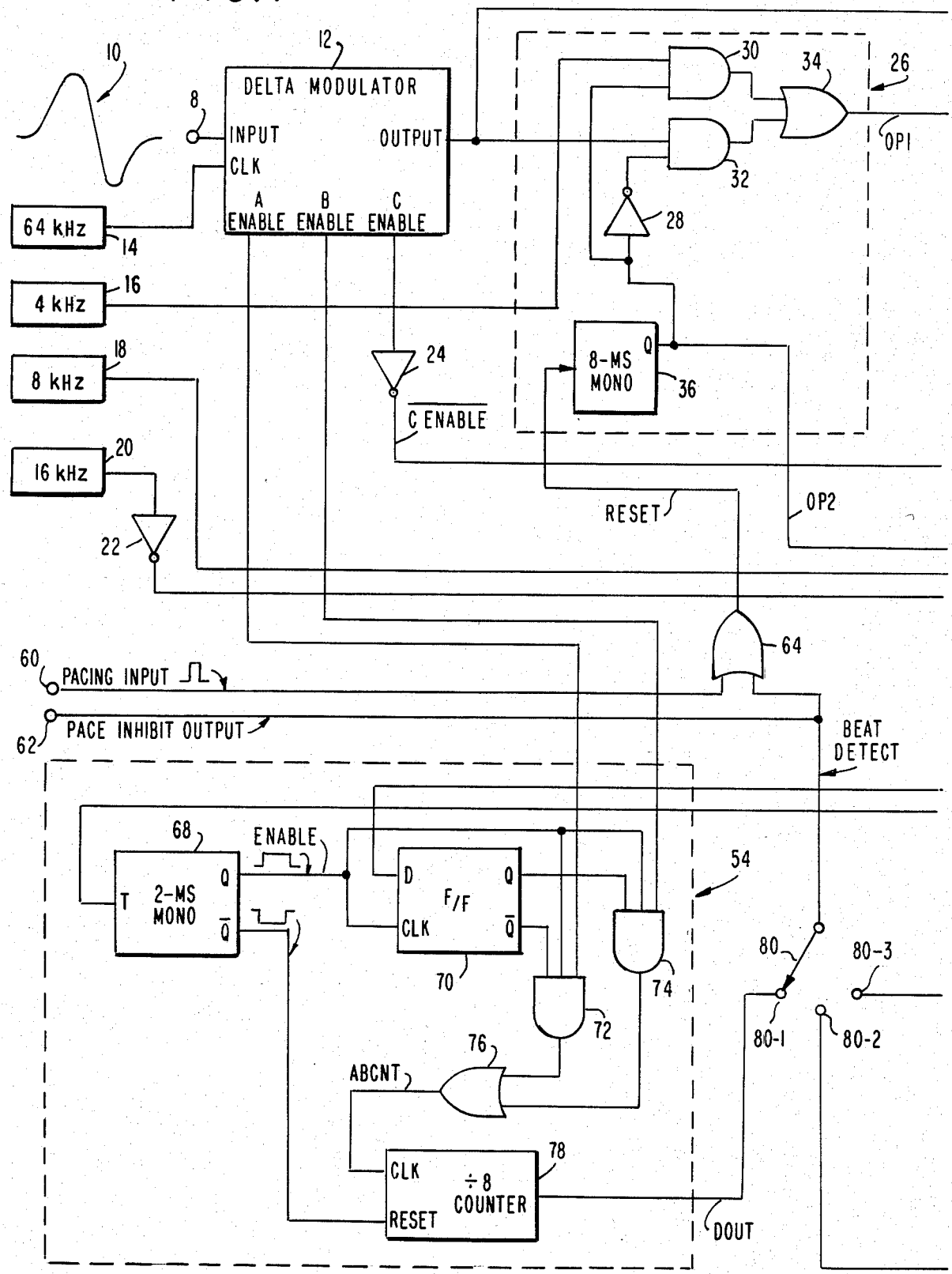

United States Patent [19]

Money et al.

[11] Patent Number: 4,509,529
[45] Date of Patent: Apr. 9, 1985

[54] PHYSIOLOGICAL EVENT RECOGNITION TECHNIQUES FOR USE WITH A DELTA MODULATOR

[75] Inventors: David K. Money, Pennant Hills; Stephen Swift, Hornsby; Andrew MacLaurin, North Epping; John G. Frost, West Pymble, all of Australia

[73] Assignee: Telectronics Pty. Ltd., Lane Cove, Australia

[21] Appl. No.: 393,649

[22] Filed: Jun. 30, 1982

[51] Int. Cl.³ .............................................. A61B 5/04
[52] U.S. Cl. .................................................... 128/708
[58] Field of Search ........................ 128/696, 702–704, 128/708, 710; 364/415, 417, 138, 193; 332/11 D; 375/28; 340/352

[56] References Cited

U.S. PATENT DOCUMENTS

| | | | |
|---|---|---|---|
| 3,868,567 | 2/1975 | Ekstrom | 128/704 |
| 3,952,731 | 4/1976 | Worstencroft | 128/702 |
| 4,388,927 | 6/1983 | Schober | 128/419 PG |

Primary Examiner—William E. Kamm
Attorney, Agent, or Firm—Gottlieb, Rackman & Reisman

[57] ABSTRACT

The signal sensed on a heart pacer electrode is converted by a delta modulator to a sequence of samples of 0 and 1 bit values. The resulting bit sequence is delayed, and the original bit sequence and its delayed version are continuously subtracted from each other in a clocked up/down counter to derive a count. When the count reaches a threshold value, three different recognition logic circuits are triggered and they then operate for two milliseconds. One circuit recognizes a beat if the count does not drop below another, lower threshold value during the timing interval. A second circuit detects a beat if the count remains above the threshold level for at least 50% of the time during the timing interval. The third circuit detects a beat by operating directly on the delta modulator output bit sequence; it checks whether bits of the value indicative of the triggering event predominate over bits of the opposite value during the timing interval.

31 Claims, 4 Drawing Figures

PHYSIOLOGICAL EVENT RECOGNITION TECHNIQUES FOR USE WITH A DELTA MODULATOR

DESCRIPTION

This invention relates to delta modulators for processing internal physiological signals sensed by an implantable medical prosthesis, and more particularly to logic circuits for operating on the output of a delta modulator to recognize events of interest represented in a physiological signal.

In the copending application of Money et al entitled "Time-Domain Processing of Internal Physiological Signals", Ser. No. 320,338 filed on Nov. 12, 1981, now U.S. Pat. No. 4,466,440 which issued on Aug. 21, 1984, which application is hereby incorporated by reference, there is disclosed a delta modulator which allows time-domain processing of internal physiological signals. The use of such a modulator permits digital time domain or frequency domain processing of analog physiological signals, even in the input stage of a heart pacer, for example, rather than conventional analog frequency-domain processing. The input signal is converted to a bit stream which, in addition to being operated upon within the pacer, can be transmitted to an external monitor; the bit stream can be used to form an accurate reconstruction of the sensed signal.

The delta modulator disclosed in said copending application in effect tracks the analog signal being monitored. A continuous sequence of bit samples is generated, the two states of the bit samples representing changes in respective opposite directions in the sensed signal. If the input signal starts to change in one direction, a sequence of bits with an excess of one value will be generated by the delta modulator; a change in the input signal in the opposite direction causes a sequence of bits with an excess of opposite value to be generated. The input signal to the delta modulator can be reconstructed by causing a fixed-size step to be taken for each received bit sample, the direction of the step depending upon the bit-sample value. Once the input signal settles down to a quiescent level, and after the delta modulator has caught up to the input signal, bit samples of alternating values are generated. An excess of bit samples of the same value are then generated only after the input signal starts to change. As long as the delta modulator operates at a fast enough rate, the reconstructed signal will accurately follow the input signal.

However, it is also important that the delta modulator not operate at too fast a rate. In the Money et al system, a cardiac event of interest (e.g., a P wave or an R wave) is recognized by four successive output samples of the delta modulator having the same value. A sequence of bit samples of the same value can be generated for a signal which continuously changes in the same direction if there is a lag in the modulator response. It is because the modulator bit samples must "catch up" to the changing input signal that a sequence of sample bits of the same value is generated. A practical delta modulator, therefore, must be slew-rate limited; it is a "slope overload" that gives rise to a sequence of bit samples of the same value while the modulator catches up to the input signal. A basic problem with such a slew-rate limited delta modulator is that the bit sample sequence generated by the device is not a true digital representation of the analog input, and it does not allow a true replica of the input signal to be reconstructed from the bit samples. If the clock rate of the modulator is increased so that the input signal can be tracked accurately, a different method of detecting the event of interest must be used; noise signals may also be tracked and a noise spike may be "recognized" as an event of interest.

There is still another problem which is peculiar to the use of a delta modulator when monitoring signals such as a cardiac signal, especially where the event of interest to be recognized is the occurrence of a P wave. A P wave typically has an amplitude as low as about 300 microvolts. Following the generation of a pacing pulse, if the delta modulator is incorporated in an implantable heart pacer, repolarization of the electrode-tissue interface results in the generation of a signal which is very large in magnitude and can overload the input of the delta modulator. This means that while the modulator catches up to the input signal, small signals such as a P wave which appear on the repolarization waveform may not be detected. Following the generation of a pacing pulse, especially in a dual-chamber pacer where atrial beats must be recognized, it should be possible to detect P waves by the time approximately 100 milliseconds have elapsed following the generation of a pacing pulse. But it is difficult to detect P waves with prior art delta modulators and recognition logic circuits due to overloading effects.

It is a general object of our invention to provide recognition logic circuits for use with a delta modulator, and particularly a delta modulator for operating on a sensed cardiac signal, which allow events of interest to be recognized in the presence of the electrode recovery or repolarization waveform, and without the modulator being excessively slew-rate limited to the point at which tracking of the sensed signal is inaccurate. (With use of the illustrative embodiment of the invention, all but very fast changing waveforms can be tracked accurately; tracking becomes inaccurate only when the sensed signal changes at a rate greater than about 0.65 volts per second, well above the rate at which typical cardiac signals change. At the same time, the recognition logic circuits are relatively immune to noise.)

The illustrative embodiment of our invention utilizes a delta modulator such as that shown in the Money et al application. The delta modulator itself will be described below only in terms of its input and output signals, and some of the additional timing signals which are generated internally. The details of the delta modulator are not important for an understanding of the present invention. The major difference between the Money et al delta modulator and that incorporated in the illustrative embodiment of our invention is the sampling rate; in our invention the sampling rate is increased from 500 Hz to 8 kHz in order to allow more accurate tracking of the input signal. Our invention concerns how events of interest can still be recognized even in the presence of noise in the input signal and the electrode recovery waveform.

In the Money et al delta modulator, the analog signal appears at an input terminal, and a bit sequence appears at the output terminal. The input signal is coupled through a capacitor to the plus input of a comparator, the minus input of the comparator being connected to a reference potential. Suppose, for example, that the input signal starts to increase from some quiescent level. This tends to cause the potential at the plus input of the comparator to rise, and the output of the comparator switches to a respective state. This state of the output causes a first current source to control a current flow through the input capacitor which tends to restore the potential at the plus input of the comparator to the reference potential. In a similar manner, and in response to the modulator output being in the opposite state, another current source controls a current flow through the capacitor in the opposite direction when the input signal decreases from a quiescent level. The entire operation is clocked so that output bit samples are derived at a constant rate, with output bits of different values causing equal-magnitude but oppositely poled voltage steps across the input capacitor. In the case of a constant or non-changing input, alternating 0 and 1 bit values appear at the delta modulator output.

The delta modulator does not function to cause the potential at the plus input of the comparator to track that at the input terminal. The comparator plus input is a virtual ground at the reference potential applied to the minus input. What happens is that the input capacitor is charged and discharged by the two current sources so that the potential at the input terminal has added to it or subtracted from it a capacitor potential such that the resulting level at the plus input of the comparator equals the reference potential.

In accordance with the principles of our invention, and in the illustrative embodiment thereof, the bit sample sequence at the output of a heart pacer delta modulator is fed into a digital delay line, the output of which is a delayed version or replica of the original sequence. A counter is provided for deriving a count which is indicative of differences between the two bit sample sequences. An on-going difference count is formed by alternately feeding one of the original and delayed bit sample sequences, and an inversion of the other, to the up/down input of a clocked up/down counter.

Three different recognition logic circuits are provided, all of which are responsive to the count for indicating an event of interest. The first recognition logic circuit is triggered by the count in the counter reaching a first predetermined value. (The word "count" here means the absolute magnitude of a count which can be positive or negative, as will become apparent below.) Following this triggering event, the recognition logic circuit determines whether the count passes a second, different predetermined value; in the illustrative embodiment of the invention, as long as the count does not fall below a second, lower predetermined value within two milliseconds of the count first reaching the first predetermined value, it is assumed that a P wave or an R wave is present in the input signal.

The second recognition logic circuit is similarly triggered by the count reaching a predetermined value. It generates an output indicative of an event of interest if during a two-millisecond interval following triggering of the circuit, the count is at or above a predetermined value for some total predetermined time. In the illustrative embodiment of the invention, this predetermined value is the same as the value of the count which triggers the circuit in the first place and the total predetermined time is one millisecond.

The third recognition logic circuit is triggered in the same way, by the counter count reaching a predetermined value. But the third recognition logic circuit then directly monitors bit sample outputs of the delta modulator for a two-millisecond timing interval. An indication of a cardiac event of interest is generated if the ratio of the number of bit samples of the state which gave rise to the triggering of the circuit to the number of bit samples of the opposite state exceeds a predetermined value. In other words, during the two-millisecond timing interval and with a delta modulator operating at a fixed clock rate, the number of bit samples of the state which gave rise to the initial threshold count must exceed a predetermined number for an assumption to be made that a P wave or an R wave is reflected in the input signal.

Following the detection of a beat, i.e., a P wave or an R wave, the system is reset by resetting the counter to zero and by initializing the delayed output bit sample sequence with a predetermined number of bit samples of alternating states. In effect, the delayed bit sample sequence is made to represent a non-changing input. In this manner, the subtraction operation which is effected by the counter can begin to compare the output of the delta modulator with an output which would ordinarily have been derived for a non-changing input.

Figure 2:
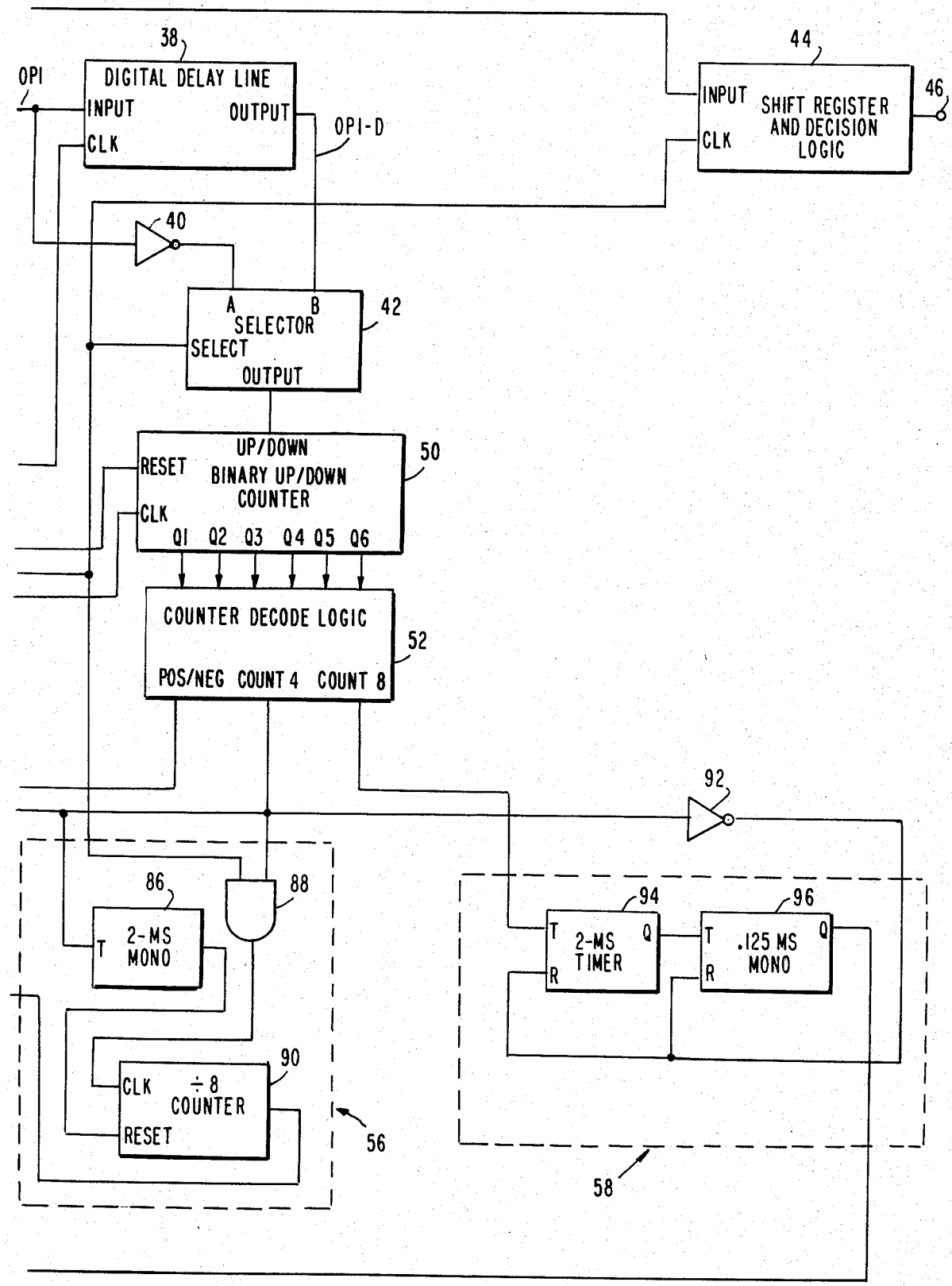
Figure 3:
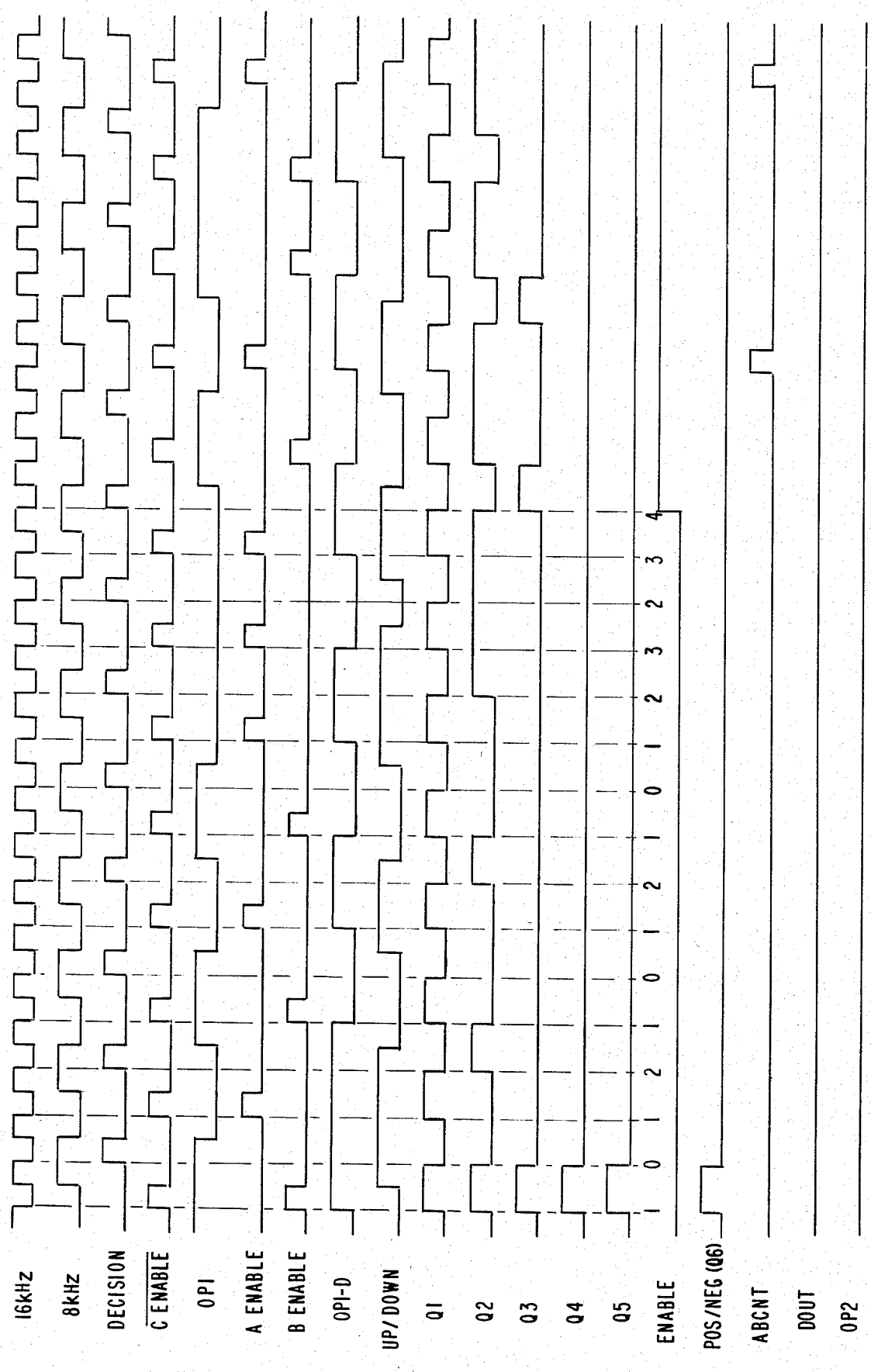
Figure 4:
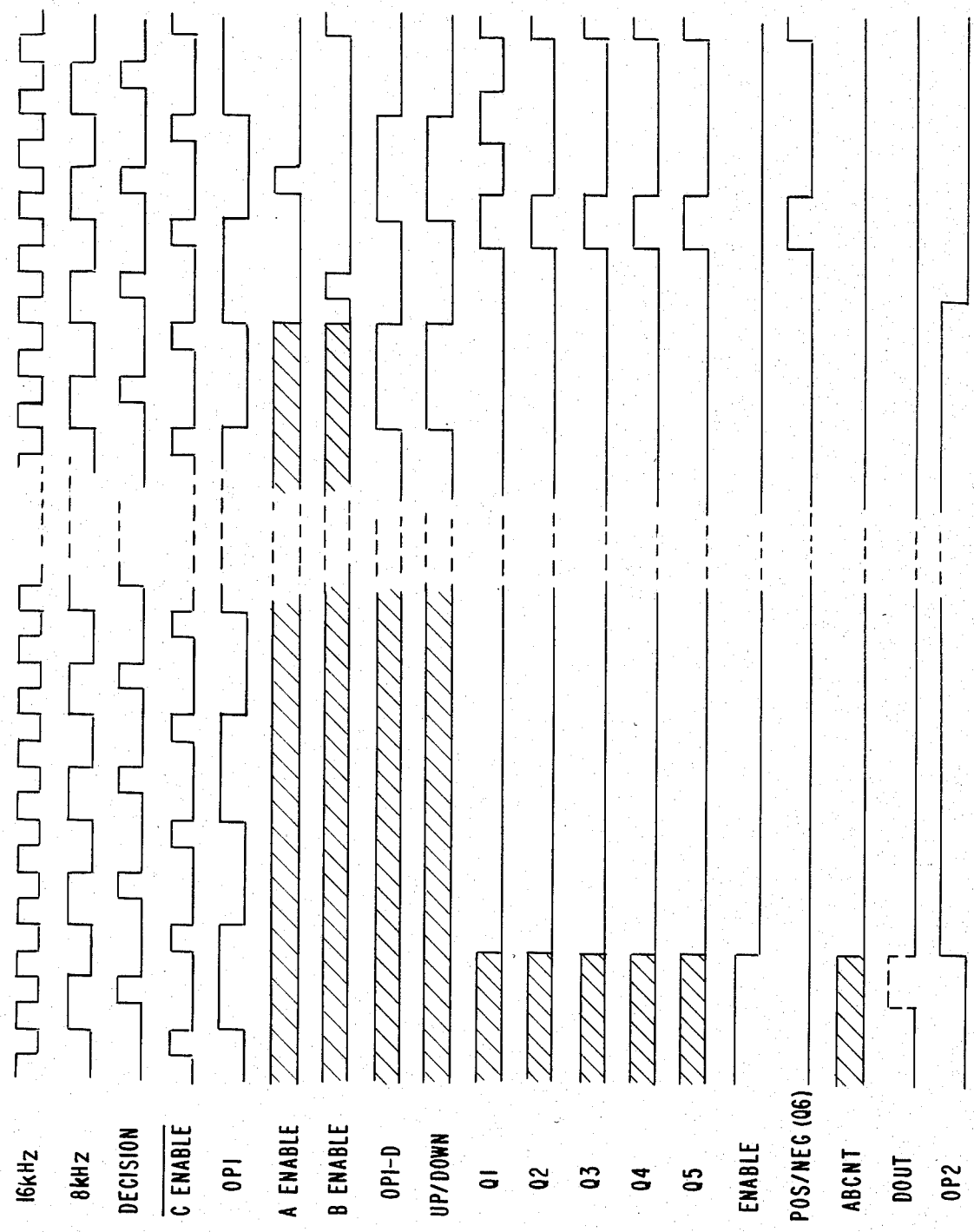

Further objects, features and advantages of our invention will become apparent upon consideration of the following detailed description in conjunction with the drawing, in which:

FIGS. 1 and 2, with FIG. 1 being placed to the left of FIG. 2, depict the illustrative embodiment of the invention for operating in conjunction with a heart pacer;

FIG. 3 is a set of waveforms which characterize the system operation over a certain time interal; and FIG. 4 is a comparable set of waveforms which characterize the system operation over a subsequent time interval.

The system of FIGS. 1 and 2 is designed to work with a conventional heart pacer. The pacer itself is not shown inasmuch as the present invention is self-contained, has general utility, and the source of the physiological signal to be monitored and analyzed is not important for an understanding of the invention. The system is shown as interfacing to the heart pacer at three terminals. The physiological signal to be monitored is applied to input terminal 8 of delta modulator 12; a typical signal is shown by the numeral 10, and it can be derived in a wellknown manner from a stimulating electrode. The pacer applies a "pacing input" pulse at terminal 60 in FIG. 1 whenever it generates a pacing pulse. The reason for providing such an input is that the recognition logic should be reset following the generation of a pacing pulse prior to subsequent monitoring of the signal on the pacer electrode.

The recognition logic of FIGS. 1 and 2 is used to determine the presence of a heartbeat signal, typically a waveform such as waveform 10 which results from a spontaneous beat. When a beat is detected, a "pace inhibit output" pulse is applied at terminal 62. This terminal is connected to the heart pacer, and a pulse appearing at the terminal resets the timing circuit of the pacer to indicate that a spontaneous beat has been detected.

Insofar as the circuit of FIGS. 1 and 2 is concerned, the source of the electrode signal to be monitored is unimportant; the circuit can even be used in non-pacer applications. As for a "pacing input" pulse at terminal 60, a signal appearing at this terminal can simply be thought of as a reset input to the system of FIGS. 1 and 2. As for the pace inhibit output pulse, at terminal 62, it is simply an indication that an event of interest has been detected. What is done with the output pulse depends upon the device with which the system of FIGS. 1 and 2 operates.

The delta modulator block 12 is not shown in detail in FIG. 1. It is shown and described in detail in the above-identified Money et al application. All that is required is to understand its input and output signals. The input signal is the signal to be monitored and analyzed, and the output signal is a sequence of 1 and 0 sample values, represented as high and low potentials. The output waveform changes, when it does, at the sampling rate, 8 kHz in the illustrative embodiment of the invention. This requires a 64-kHz input clock. The clock which is used in the Money et al system is only a 4-kHz clock. A clock rate 16 times higher is used in the illustrative embodiment of the invention in order to increase the slew rate capability of the delta modulator. The A ENABLE, B ENABLE and C ENABLE output signals of the delta modulator are the same as those described in the Money et al application except that they occur at rates 16 times higher due to the use of a faster system clock. In FIG. 1, four clocks 14, 16, 18 and 20 are shown, having respective rates of 64, 4, 8 and 16 kHz. The three lower clock frequencies are derived from the basic 64-kHz clock simply by the use of a chain of divide-by-two counters, as is known in the art. Each clock waveform changes on a rising edge in the output of the next higher clock waveform.

The output of the delta modulator is extended to the input of shift register and decision logic block 44. This block corresponds to the logic disclosed in the Money et al application. The clock input of block 44 is pulsed at the sampling rate (8 kHz as opposed to 500 Hz in the Money et al system). The output samples from the delta modulator are serially inputted to the shift register in block 44. The logic in the block looks for four successive 0 or 1 bit values to determine the presence of a heartbeat, resulting in an output pulse at terminal 46.

As described above, the problem with this approach is that in order both to be immune from noise and to ensure that four successive samples have the same value for a changing input signal, the delta modulator must be slew-rate limited. But with a slew-rate limited delta modulator, the output samples do not closely track the input signal. If the input signal changes rapidly before the signal reconstructed from the output samples has caught up to it, the rapid change, e.g., a low-level pulse superimposed on a large signal swing, will be missed because the system cannot respond to rapid changes in the input. It is for this reason that we utilize a higher sampling rate even in a system having the same or similar step size as in the Money et al system. However, while this allows rapidly changing signals to be tracked, it also means that noise present in the input signal is reflected in the output bit sequence. In a slew-rate limited system, the effect of high-frequency noise is effectively reduced because the reconstructed output signal lags the input signal, and the reconstructed output signal in effect "misses" rapid changes in the input signal resulting from the noise. With a fast sampling rate, however, the reconstructed output signal (or, more accurately, the delta modulator output samples which represent the signal) more closely tracks the input signal. Thus noise in the input signal can quite readily result in a succession of bit samples of the same value. Were the prior art block 44 to be utilized with a fast sampling rate, false indications of heartbeats would result from noise in the input. In addition, the signal voltage required to indicate a heartbeat would be considerably greater. The purpose of the circuit of FIGS. 1 and 2 is to allow samples to be generated at a rate sufficient to allow accurate tracking of the input signal, including any noise which appears in the input signal (except for very high-frequency noise), while still ensuring that noise in the input signal will not result in the erroneous detection of a heartbeat.

The clocked samples at the output of delta modulator 12 are applied to an input of gate 32 in block 26. This block serves to extend to output conductor OP1 either the waveform at the output of the delta modulator or a 4-kHz signal from clock 16. The output of 8-millisecond monostable multivibrator 36 is ordinarily low; gate 30 is disabled while inverter 28 enables gate 32. It is thus apparent that while the multivibrator is reset, the output waveform from the delta modulator is extended through gate 32 and OR gate 34 to output conductor OP1. It is only when the multivibrator is triggered, by a system reset signal at the output of OR gate 64, that the Q output goes high to disable gate 32 and to enable gate 30. At this time, the 4-kHz clock signals appear on output conductor OP1.

Digital delay line 38 is simply a sequence of 32 flip-flops arranged as a shift register. The bit samples on conductor OP1, appearing at the input of the digital delay line, are clocked by the $\overline{\text{C ENABLE}}$ signal at the output of inverter 24. The C ENABLE signal is generated by the delta modulator, as will be described shortly, and consists of negative pulses occurring at an 8-kHz rate. Consequently, for every bit sample from delta modulator 12 which is extended through gate 32 to the OP1 conductor, a clock pulse is generated for storing the sample in the digital delay line. The 32 samples contained in the delay line at any time reflect the last 32 samples generated at the output of the delta modulator. On the other hand, while the system is being reset and gate 30 is enabled, a 4-kHz waveform appears on the OP1 conductor, while the delay line is clocked by pulses occurring at an 8-kHz rate. Thus each half of the 4-kHz clock signal controls the storage of a bit in the delay line. After 32 C ENABLE pulses have been generated by the delta modulator, the digital delay line contains 32 alternating 0 and 1 bits. Monostable multivibrator 36 controls the storage of alternating 0 and 1 bit values in the delay line for 8 milliseconds, and since it is a 4-kHz clock signal which is applied to the input of the delay line while the system is being reset, 64 bits of alternating value are actually stored in the delay line during the reset procedure. Thus by the middle of the reset sequence, not to mention the end, the delay line is filled with alternating bit values.

As described in the Money et al application, the delta modulator generates three signals, A ENABLE, B ENABLE and C ENABLE. The C ENABLE output is ordinarily high, but a short negative pulse is generated during each cycle of operation of the delta modulator, i.e., at the sampling rate. Each of the A ENABLE and B ENABLE outputs is ordinarily low, but a positive pulse appears at one of these two outputs coincident with the negative C ENABLE pulse. The A ENABLE and B ENABLE pulses represent a current bit sample of different values. For an input signal which is decreasing, an A ENABLE pulse is generated. For an input signal which is increasing, a B ENABLE pulse is generated.

With these remarks in mind, the first few waveforms in FIG. 3 can be understood. The first two waveforms simply depict two system clocks, at respective rates of 16 kHz and 8 kHz. The third waveform, the DECISION signal, is not necessary for an understanding of the present invention, although it does help to clarify the operation of the Money et al delta modulator. The DECISION pulses represent the taking of samples, at an 8-kHz rate, each sample value being determined at the trailing edge of the pulse. The fourth waveform in FIG. 3 is the $\overline{\text{C ENABLE}}$ signal; each pulse in this waveform occurs subsequent to a corresponding DECISION pulse.

The fifth waveform in FIG. 3 is the OP1 signal in FIG. 1. As long as the delta modulator is tracking an input signal and monostable multivibrator 36 is reset, the OP1 signal is the same as the signal at the output of the delta modulator. The OP1 signal is thus shown in FIG. 3 as changing at an 8-kHz rate. It will be noted that the first five samples alternate in polarity to indicate a non-changing input signal.

As mentioned above, the A ENABLE output of the delta modulator is pulsed coincident with the generation of a $\overline{\text{C ENABLE}}$ pulse, whenever the current sample represents a decreasing input signal. Thus the A ENABLE waveform in FIG. 3 is shown as having a positive pulse, coincident with a $\overline{\text{C ENABLE}}$ pulse, whenever the OP1 signal is low. Similarly, a B ENABLE pulse is generated, coincident with a $\overline{\text{C ENABLE}}$ pulse, if the OP1 signal is high.

The OP1-D signal at the output of digital delay line 38 is the same as the OP1 input signal, except that it is delayed by the time taken for a bit to be shifted through the 32 stages of the block. Since the delay line is clocked by the $\overline{\text{C ENABLE}}$ 8-kHz pulses, which are separated by 0.125 milliseconds, it is apparent that the delay introduced by block 38 is $(32) \times (0.125$ milliseconds$)$ or 4 milliseconds. (As mentioned above, this is why the delay line is filled up with alternating 0 and 1 bits by the time the middle of an 8-millisecond reset sequence has been reached.) The OP1-D waveform in FIG. 3 thus represents the waveform at the output of the delta modulator which occurred 4 milliseconds, or 32 sample times, earlier.

Before discussing selector 42, an important timing characteristic of the OP1 and OP1-D waveforms should be appreciated. The OP1 signal, corresponding to the output of the delta modulator, can change on the falling edge of a DECISION pulse. The delta modulator output changes before the $\overline{\text{C ENABLE}}$ pulse, and either the A ENABLE or B ENABLE pulse, are generated so that a sample is actually available prior to the generation of the ENABLE pulses. The A ENABLE and B ENABLE pulses control charging of the input capacitor of the delta modulator in opposite directions, and thus the current sample at the output of the modulator must be available prior to generation of the $\overline{\text{C ENABLE}}$ pulse. But the digital delay line 38 is clocked by $\overline{\text{C ENABLE}}$ pulses, and this means that changes in the OP1-D waveform occur at the leading edge of each $\overline{\text{C ENABLE}}$ pulse shown in the fourth waveform of FIG. 3. Thus as is apparent from the OP1 and OP1-D waveforms in FIG. 3, not only is the OP1-D waveform delayed by 32 8-kHz clock times from the OP1 signal, but the OP1-D waveform is further delayed by one-quarter of an 8-kHz clock cycle. In other words, the two signals are not only delayed relative to each other by 32 clock cycles, but they are also slightly out of phase.

Selector 42 is provided with two inputs. The OP1 input is inverted by inverter 40 and applied to the A input while the OP1-D signal is applied directly to the B input. The select input of the selector is controlled by the 8-kHz clock. When the select input is high, the OP1-D input to selector 42 is extended through the selector to the output; when the select input is low, the inverted OP1 input to the selector is extended through the device to the output. Thus for half of each 8-kHz clock cycle one of the two inputs appears at the output of the selector, while during the other half of the cycle the other input appears at the output. The output of the selector is extended to the up/down input of counter 50, and the waveform at the up/down input of the counter is shown in the ninth line of FIG. 3.

Suppose that the OP1 and OP1-D signals are identical, e.g., the input signal to the delta modulator is not changing so that alternating bit samples are generated. While the OP1-D signal is delayed relative to the OP1 signal, the two of them are identical since one is simply delayed relative to the other by 32 sample times. Because inverter 40 inverts the OP1 signal before it is applied to the A input of selector 42, and the two selector inputs are selected in succession during each 8-kHz clock period, it is apparent that the two inputs to selector 42 are always opposite in value during each clock period for a non-changing input. This simply means that the output alternates in polarity during the two halves of each 8-kHz clock cycle. The reason for the additional phase shift between the OP1-D and OP1 signals is now apparent; during each 8-kHz clock cycle, the OP1 signal is to control the output of the selector for half the time, and the OP1-D signal is to control the output of the selector for the other half of the time. By causing the two signals to be out of phase, each signal can control the output of the selector during a respective half of each 8-kHz clock cycle. For a non-changing input, the up/down waveform is simply a square wave with a duty cycle of 1:1. Since the sampling rate is 8 kHz, the output of the delta modulator is high for one clock cycle, low for the next, then high again, etc. This corresponds to a square-wave output of the delta modulator at a 4-kHz rate. This is the same rate at which the symmetrical up/down waveform is generated for a non-changing input, resulting in no overall change in the count; the count alternately increments and decrements.

For a changing input, however, the OP1 waveform has bits of one value which predominate while the earlier-based OP1-D waveform has bits of alternating values; the up/down signal remains constant for the entire durations of some 8-kHz clock cycles. Thus if the OP1 and OP1-D signals are different, as they are in FIG. 3, the up/down waveform is no longer symmetrical. The up/down waveform of FIG. 3 is derived in a straightforward manner. Whenever the 8-kHz clock signal is high, the up/down signal follows the OP1-D waveform. Whenever the 8-kHz clock waveform is low, the up/down waveform follows the inverse of the OP1 waveform. It is apparent from the waveform shown in FIG. 3 that the up/down input of counter 50 is high on average more than it is low, corresponding to a decreasing signal at the input of delta modulator 12.

Binary up/down counter 50 has six outputs Q1–Q6. All of the outputs are reset to zero when the reset input of the counter is pulsed high during the 8 milliseconds that the Q output of multivibrator 36 is high when the system is being reset. If the reset input is low, however, the counter counts up or down each time that a clock pulse is applied to the clock input, the counter counting up or down depending on the state of the up/down input. The clock pulses are derived from 16-kHz clock 20, through inverter 22; thus the counter changes state on each falling edge of the 16-kHz waveform in FIG. 3

(right in the middle of each select phase of selector 42). With the Q1 bit being the least significant and the Q6 bit being the most significant, the Q6 bit represents the sign of the count (in 2's complement arithmetic), as is well known in the art. The following table depicts the counter operation:

| Decimal Value | Q6 | Q5 | Q4 | Q3 | Q2 | Q1 |
|---|---|---|---|---|---|---|
| +31 | 0 | 1 | 1 | 1 | 1 | 1 |
| ... | | | ... | | | |
| +4 | 0 | 0 | 0 | 1 | 0 | 0 |
| ... | | | | | | |
| 0 | 0 | 0 | 0 | 0 | 0 | 0 |
| −1 | 1 | 1 | 1 | 1 | 1 | 1 |
| −2 | 1 | 1 | 1 | 1 | 1 | 0 |
| ... | | | ... | | | |
| −32 | 1 | 0 | 0 | 0 | 0 | 0 |

The Q1–Q5 waveforms in FIG. 3 represent the five least significant bit outputs of counter 50. Underneath the Q5 waveform, coincident with each falling edge of the 16-kHz clock waveform when the state of the counter changes, there is shown the new count represented by the counter. Negative values correspond to a Q6 bit of value 1 and positive values correspond to a Q6 bit of value 0. It is assumed that the counter is initially reset so that all of the Q1–Q5 bits have 0 values. The counter is arranged such that a positive step in any bit output changes the state of the next succeeding stage. The first time that the counter is clocked, the up/down input is low. This means that the counter counts down to represent a count of −1, and in accordance with the table represented above all of the Q1–Q5 outputs go high as shown in FIG. 3. When the counter is clocked for the second time, the up/down input is high; the counter now counts up to represent a value of 0 as shown in FIG. 3, with all of the Q1–Q5 outputs going low.

The up/down signal is still high during the next two clockings of the counter. Consequently, the count first advances to +1 decimal (000001), and then advances to +2 decimal (000010). Since the up/down input is low when the next clock pulse is generated, the count is next decremented. In a similar manner, the numbers underneath the Q5 waveform in FIG. 3 illustrate how the count advances to a value of +4. It is at this time that the three recognition logic circuits to be described below go into action. The rapid increase in the count toward the end of the counting sequence depicted in FIG. 3 is due to the OP1 signal being low more often than it is high. Thus it is apparent that positive counts correspond to decreasing input signals (when more A ENABLE pulses are generated by the delta modulator than B ENABLE pulses, the significance of which will become apparent below).

Counter decode logic 52 analyzes the Q1–Q6 outputs of counter 50. The POS/NEG output of logic circuit 52 is simply the counter Q6 bit; this logic output is high for negative counts and low for positive counts. The COUNT 4 output of logic circuit 52 is high whenever the count represented by counter 50 has an absolute magnitude of 4 or greater. Thus the COUNT 4 output is high whenever the count represented by the counter is between 4 and 31, or between −4 and −32. In a similar manner, the COUNT 8 output of logic circuit 52 is high whenever the count is greater than 8 or less than −8. Since the three recognition logic circuits to be described respond to both increasing and decreasing input signals, what is important is the absolute magnitude of the count, not whether it is positive or negative.

The first recognition logic circuit is shown within dashed lines 56. When the COUNT 4 output of logic circuit 52 goes high, gate 88 is enabled. The other input to this gate is connected to the 8-kHz clock, so that the clock pulses are extended through the gate to the input of divide-by-eight counter 90. The COUNT 4 output of logic circuit 52 is also extended to the trigger input of 2-millisecond timer 86. The output of the timer is ordinarily high and, because it is connected to the reset input of divide-by-eight counter 90, it holds the counter reset. Once the timer is triggered, however, a 2-millisecond negative pulse appears at its output so that counter 90 can count the 8-kHz clock pulses extended through gate 88.

During the two milliseconds between the time that gate 88 is first enabled by the COUNT 4 output of logic circuit 52 and the resetting of divide-by-eight counter 90, and since the clock pulses extended through gate 88 occur at an 8-kHz rate, 16 clock pulses are generated. If the COUNT 4 output of logic circuit 52 remains high for at least 50% of the time during the 2-millisecond timing interval, at least 8 clock pulses are extended to the clock input of counter 90, and after 8 clock pulses have been counted the output is pulsed high. The output of the counter is connected to terminal 80-3 of connector switch 80. Selector switch 80 is provided so that any one of the three alternative recognition logic circuits can be selected to generate the "beat detect" signal. If the selector switch is connected to terminal 80-3, the positive pulse at the output of counter 90 is extended to the BEAT DETECT conductor. Not only is the positive pulse extended to the pace inhibit output terminal 62 for reasons described above, it is also extended through OR gate 64 to the rest input of multivibrator 36. On the falling edge of the pulse the multivibrator is triggered; its output goes high for 8 milliseconds to reset the entire system, during which time alternate 0 and 1 bit values are stored in delay line 38.

For a non-changing input, as described above the up/down input of counter 50 has a 1:1 duty cycle. It will be recalled that counter 50 is clocked at a 16-kHz rate. The OP1 and OP1-D signals cancel each other out in the counter if they represent equal bit values. Thus it requires two 16-kHz clock cycles for the count in counter 50 to be incremented and then decremented, or decremented and then incremented, corresponding to a single sample which appears at the output of the delta modulator during an 8-kHz clock cycle. Counter 90 is clocked at an 8-kHz rate so that no changes occur in the outputs of logic circuit 52 for a non-changing input.

During the two milliseconds that counter 90 is enabled to count 8-kHz clock pulses, a total of 16 pulses may be counted. If the COUNT 4 output of logic circuit 52 is high throughout the 2-millisecond interval, all 16 pulses will be counted. On the other hand, if it is not high continuously, fewer of these pulses will be counted. But as long as the COUNT 4 output of the logic circuit is high for a total of one millisecond during the 2-millisecond timing interval (which one millisecond need not be continuous), at least 8 clock pulses will be counted and recognition logic circuit 56 will generate an output pulse to indicate the detection of a beat. Thus the test performed by recognition logic circuit 56 is whether the count in counter 50 remains equal to or above the threshold count which triggers a timing interval for a predetermined fraction (0.5 in the illustrative embodiment of the invention) of the timing interval. (The COUNT 8 output of logic circuit 52 is not utilized by recognition logic circuit 56, nor by recognition logic circuit 54; it is utilized only by recognition logic circuit 58.)

Recognition logic circuit 58 includes a 2-millisecond monostable multivibrator 94 which is ordinarily held reset; the low COUNT 4 output of logic circuit 52 is inverted by inverter 92 and a positive potential is extended to the reset input of the multivibrator. As soon as the COUNT 4 output goes high, however, the output of inverter 92 goes low so that the reset input is lifted from the multivibrator. No other action takes place, however, because the multivibrator is not actually triggered.

The multivibrator is triggered only when the COUNT 8 output of counter 52 first goes high. The Q output of the multivibrator goes high, and it goes low once again only at the end of the 2-millisecond timing interval. The falling edge triggers multivibrator 96 which then generates a short 0.125-millisecond pulse at its Q output. The pulse at the output of multivibrator 96 is extended to terminal 80-2 so that if selector switch 80 is connected to this terminal a "beat detect" indication is obtained.

If at any time during the 2-millisecond timing interval the COUNT 4 output of logic circuit 52 goes low, multivibrator 94 is reset; an output pulse is not generated by multivibrator 96 at this time because it is also held reset. Thus the recognition test consists of starting a timing interval when a count of 8 is reached, and checking that the count does not drop down to 4 by the end of the timing interval.

Recognition logic circuit 54 is more complicated than the other two, and for this reason some additional waveforms which relate to this circuit are shown in FIG. 3. When the COUNT 4 output of logic circuit 52 first goes high, 2-millisecond monostable multivibrator 68 is triggered. A positive pulse appears at the Q output and a negative pulse appears at the $\bar{Q}$ output. Divide-by-eight counter 78 is normally held reset by the high potential at the $\bar{Q}$ output of the multivibrator, but the reset input is lifted during the 2-millisecond timing interval. The leading edge of the 2-millisecond positive ENABLE pulse at the output of multivibrator 68 clocks flip-flop 70. The POS/NEG output of logic circuit 52 is connected to the D input of the flip-flop, and consequently the output of the flip-flop which goes high depends upon the sign of the count in counter 50 when its absolute magnitude first reaches a value of 4. Each of gates 72, 74 is enabled by a different one of the multivibrator outputs, and the one enabled gate can operate for only the 2 milliseconds that the Q output of multivibrator 68 remains high since the Q output is connected to an input of each gate. The third input to each of gates 72, 74, is one of the A ENABLE and B ENABLE signals. During the 2-millisecond timing interval, one of the two gates passes respective A ENABLE or B ENABLE pulses through OR gate 76 to the ABCNT conductor which is connected to the clock input of divide-by-eight counter 78. The DOUT output of the counter, connected to terminal 80-1, is high when 8 clock pulses have been counted, to indicate the detection of a beat if selector switch 80 is connected to terminal 80-1.

It will be recalled that an increasing count in counter 50 corresponds to a decreasing input signal and the generation of A ENABLE pulses. A positive count in counter 50 (with the POS/NEG output of logic circuit 52 being low) results in the enablement of gate 72 rather than gate 74, so that it is A ENABLE pulses which appear on the ABCNT conductor. During the two milliseconds that gate 72 is enabled, delta modulator 12, which operates at an 8-kHz rate, goes through 16 cycles. If at least half of these cycles result in the generation of A ENABLE pulses, counter 78 pulses its DOUT output. Conversely, for a negative count in counter 50 representing an increasing input signal, what is looked for are at least half of the succeeding clock cycles of the delta modulator resulting in the generation of B ENABLE pulses which correspond to an input signal which continues to increase.

The test performed by recognition logic circuit 54 is whether the input signal continues to move in the same general direction for two milliseconds after it first moved sufficiently in that direction to result in a count of 4 in counter 50. In other words, the circuit checks to see whether the delta modulator continues to operate in the same direction for at least 50% of the time during an interval which immediately succeeds an initial triggering. (Instead of utilizing a time interval of two milliseconds, some other time interval could be selected. Similarly, the test could be changed so that the delta modulator must operate in the same direction for at least 60% of the time, etc. Similar remarks apply to the other recognition logic schemes; the particular time and count values employed may vary from application to application.)

The POS/NEG waveform in FIG. 3 depicts the sign of the count in counter 50. Recalling that the Q6 bit of the counter is positive for negative counts, it is apparent that the POS/NEG waveform is high only for a count of $-1$ as shown in the drawing, with the waveform being low to indicate positive counts for the remaining counts illustrated.

The ENABLE waveform, the Q output of multivibrator 68, is low until the absolute magnitude of the count in counter 50 reaches a value of 4, as described above. It then goes high for 2 milliseconds. The ENABLE waveform in FIG. 3 is shown going high as soon as the count in counter 50 reaches a value of 4. Thereafter, gate 72 transmits succeeding A ENABLE pulses to the ABCNT conductor connected to the clock input of counter 78. The ABCNT waveform in FIG. 3 is shown as containing pulses which are coincident with the A ENABLE pulses which follow the ENABLE waveform going high.

The waveforms of FIG. 4 are designed to show the continued operation of recognition logic circuit 54 after it is first triggered, the manner in which a decision as to the detection of a beat is made, and how the system resets. All of the waveforms shown in FIG. 3 are continued in FIG. 4, although some of them are not required for an understanding of this continued operation.

Once multivibrator 68 is triggered, the operation characterized by the waveforms at the right side of FIG. 3 persists for 2 milliseconds. At the end of the timing interval the ENABLE signal goes low, as shown in FIG. 4. At this time, the states of the several signals shown by hatched lines in FIG. 4 are not important. The only thing that is important is that prior to the ENABLE signal going low, counter 78 should have counted 8 ENABLE pulses. When the 8 pulses are counted, the DOUT output is pulsed high to indicate the detection of a beat. The pulse in the DOUT waveform of FIG. 4 is shown in dashed lines since it does not necessarily occur at the end of the 2-millisecond timing interval. It can occur, if it does, at any time during the last half of the 2-millisecond timing interval when the eighth A ENABLE pulse is counted.

At the trailing edge of the pulse on the DOUT conductor, multivibrator 36 is triggered. (The output pulse from any of the recognition logic circuits can trigger a reset sequence, even before the end of the respective 2-millisecond timing interval; the 2-millisecond timing interval concludes prior to the end of the 8-millisecond reset sequence.) As described above, the Q output of the multivibrator goes high for 8 milliseconds. The Q output is connected to conductor OP2, and the OP2 waveform is also shown at the bottom of FIG. 3 and FIG. 4. During the 8 milliseconds that the OP2 conductor is high in potential, counter 50 is held reset with each of the Q1–Q6 bit outputs being a 0. Also as described above, by the middle of the 8-millisecond reset interval digital delay line 38 has stored in it 32 bits of alternating values. By the end of the reset interval, the delay line still has 32 bits of alternating values. Thus when the OP2 conductor finally goes low in potential, it will be seen in FIG. 4 that all of the Q1–Q5 signals are low in potential to indicate a count of zero in counter 50. Counting then resumes, as shown in FIG. 4, in a manner comparable to that shown at the left side of FIG. 3. The counter is reset and the digital delay line is caused to represent a non-changing input signal which "occurred" during the 32 preceding operations of the delta modulator so that the system will not reflect any past history. Instead, it starts to analyze only succeeding samples generated by the delta modulator.

With this description in mind, the three recognition schemes may be compared. But the comparison requires that the function performed by counter 50 first be clearly understood. An input signal which changes linearly in one direction has a positive or negative slope, depending on the direction. A continuous sequence of 0 bit samples or 1 bit samples, for which either only A ENABLE or B ENABLE pulses are generated, corresponds to a "constant" value which can be analogized to the constant value of the first derivative (slope) of a linear input signal which is changing in one direction. For signals which change slowly relative to the sampling rate, the bit samples are not all of the same value, but either the A ENABLE or B ENABLE pulses predominate; the relative percentages of the two types of pulses are indicative of the slope or first derivative of the input signal. Because the two inputs to selector 42 are the same, except that one is delayed relative to the other and one is inverted, what is really happening is that counter 50 maintains a running count indicative of the difference between the numbers of A ENABLE and B ENABLE pulses which are generated; the count in the counter is thus analogous to the second derivative of the input signal. All of the circuitry leading up to decode logic circuit 52 can be thought of in terms of a quasi-double differentiator.

Recognition logic circuit 54 responds to the "doubly-differentiated" signal, when the COUNT 4 output of logic circuit 52 goes high, only to the extent of starting a timing interval. Thereafter, the circuit does not respond at all to the count represented in counter 50. Instead, it "looks" directly at the input signal, as reflected by which of the A ENABLE or B ENABLE pulses predominate. Once logic circuit 52 has determined that an initial change in a particular direction has taken place, the operation of the modulator is monitored directly to see if a sufficient change continues in this same direction for a predetermined time interval. (The "sufficiency" test can be increased beyond that of the system of FIGS. 1 and 2 by requiring counter 78 to count more than eight clock pulses before it generates an output.)

Recognition logic circuit 58 is triggered when an even greater initial change has occurred, i.e., a count of absolute magnitude of eight has been achieved. What the circuit then does is to check whether this initial change was due to noise in the input. Any noise which is present should have a duration of less than two milliseconds. If the COUNT 8 output of logic circuit 52 went high originally because of noise in the input, the absolute magnitude of the count in counter 50 will fall not only below eight, but even below four during the succeeding two milliseconds. Thus if the COUNT 4 output of decode logic circuit 52 goes low within two milliseconds following the COUNT 8 output going high, it is an indication that the original relatively high count was due to noise.

Noise in the input signal can give rise to large spikes in derivatives of the signal. Recognition logic circuit 54 is less prone to provide beat indications due to the presence of noise than is recognition logic circuit 58; the former is influenced to a much lesser degree by input variations which are enhanced by quasi-double differentiation. Circuit 54 is triggered by the count in counter 50, but thereafter examines the input signal in a more direct manner, whereas circuit 58 continues to operate on the count in counter 50 even after it is initially triggered.

On the other hand, in one respect circuit 58 is less affected by noise than is circuit 54. Noise in the input signal is reflected in the OP1-D waveform as well as the OP1 waveform, and selector 42 and counter 50 perform a sort of subtraction of one waveform from the other. The subtraction averages out the noise. Thus to the extent that circuit 58 responds to the count in counter 50 even after it is triggered, it is less sensitive to noise than is circuit 54; the latter circuit, once it is triggered, is not controlled by the count in counter 50 so that there is no way for noise to be averaged out through subtraction.

Recognition logic circuit 56 is triggered by the COUNT 4 output of logic circuit 52 going high, and it then operates to derive a beat indication if the COUNT 4 output remains high for at least half the time during the succeeding 2-millisecond timing interval. Its operation subsequent to triggering is therefore a function of the quasi-doubly differentiated signal which is represented by the count in counter 50, as is the operation of circuit 58. Its operation is similar to that of circuit 54, on the other hand, in that it checks to see that the event which triggered the 2-millisecond timing in the first place persists for a predetermined fraction of the time (although it responds to the count in counter 50 rather than directly to the operation of the delta modulator); this is to be contrasted with the operation of circuit 58 which checks not whether the original condition persists, but rather whether an opposite condition of sufficient magnitude has taken place.

Circuit 58 is insensitive to noise due to the hysteresis introduced by the different trigger and reset conditions. For a true signal, i.e., one which represents a heartbeat, once the COUNT 8 output of logic circuit 52 goes high, it should remain high for the entire 2-millisecond timing interval. But if noise is superimposed on the input signal, the absolute magnitude of the count in counter 50 may drop down below eight. Heartbeats can still be detected even in the presence of some noise, however, because multivibrator 94 is not reset until the absolute magnitude of the count has dropped to below four. Circuits 54 and 56 are also insensitive to noise, but for another reason. In both of these circuits, the applicable test is whether some event persists (even on an intermittent basis) for more than a predetermined fraction of the timing interval after initial triggering. In both cases, the noise averages out. In the case of circuit 56, noise is in effect subtracted out in counter 50. In the case of circuit 54, noise may cause A ENABLE or B ENABLE pulses to predominate over short periods of time, but in any 2-millisecond timing interval the two opposite effects should balance each other out.

Although the invention has been described with reference to particular embodiments, it is to be understood that these embodiments are merely illustrative of the application of the principles of the invention. For example, digital delay line 38 might be preset with bits of the same value rather than bits of alternating value. This would require an offset to be preset in counter 50, or else the recognition logic circuits would have to take an offset into account. Thus it is to be understood that numerous modifications may be made in the illustrative embodiments of the invention and other arrangements may be devised without departing from the spirit and scope of the invention.

We claim:

1. A system for recognizing a cardiac event of interest by operating on a sensed cardiac signal comprising means for deriving from said sensed signal a first continuous sequence of bit samples, the two states of said bit samples representing changes in opposite directions in the sensed signal and bit samples of alternating opposite states representing a non-changing sensed signal, means for generating a second continuous sequence of bit samples which is the same as said first sequence but delayed in time, means for deriving a count which is indicative of on-going differences between said first and second bit sample sequences, and recognition logic means responsive to said count for indicating a cardiac event of interest.

2. A system in accordance with claim 1 wherein said recognition logic means includes means for timing a predetermined time interval, means for triggering said timing means responsive to said count reaching a first predetermined value, and means for generating an output indicative of a cardiac event of interest if within said predetermined time interval following triggering of said timing means said count does not fall below a second, lower predetermined value.

3. A system in accordance with claim 1 wherein said recognition logic means includes means for timing a predetermined time interval, means for triggering said timing means responsive to said count reaching a predetermined value, and means for generating an output indicative of a cardiac event of interest if during said predetermined time interval following triggering of said timing means said count is at or above said predetermined value for a total time which is at least a predetermined fraction of said time interval.

4. A system in accordance with claim 1 wherein said recognition logic means includes means for timing a predetermined time interval, means for triggering said timing means responsive to said count reaching a predetermined value, and means for generating an output indicative of a cardiac event of interest if during said predetermined time interval followiing triggering of said timing means the ratio of the number of bit samples of the state which gave rise to said triggering to the number of bits samples of the opposite state exceeds a predetermined value.

5. A system in accordance with claim 1 wherein said count deriving means includes means for inverting one of said first and second bit sample sequences, means for counting up or down at a clocked rate depending upon the state of an input indicative of whether counting should be up or down, and means for alternately applying to said input the inverted one of said bit sample sequences and the other of said bit sample sequences.

6. A system in accordance with claim 5 further including means, following the indication of a cardiac event of interest, for initializing said second bit sample sequence with a predetermined number of bit samples of alternating states.

7. A system in accordance with claim 1 further including means, following the indication of a cardiac event of interest, for initializing said second bit sample sequence with a predetermined number of bit samples of alternating states.

8. A system for recognizing a physiological event of interest by operating on a sensed physiological signal comprising means for deriving from said sensed signal a first continuous sequence of bit samples, the two states of said bit samples representing changes in opposite directions in the sensed signal, means for generating a second continuous sequence of bit samples which is the same as said first sequence but delayed in time, means for deriving a count which is indicative of differences between said first and second bit sample sequences, and recognition logic means responsive to said count for indicating a physiological event of interest.

9. A system in accordance with claim 8 wherein said recognition logic means includes means for timing a predetermined time interval, means for triggering said timing means responsive to said count reaching a first predetermined value, and means for generating an output indicative of a physiological event of interest if within said predetermined time interval following triggering of said timing means said count does not pass a second, different predetermined value.

10. A system in accordance with claim 8 wherein said recognition logic means includes means for timing a predetermined time interval, means for triggering said timing means responsive to said count reaching a predetermined value, and means for generating an output indicative of a physiological event of interest if during said predetermined time interval following triggering of said timing means said count is at or above said predetermined value for a total predetermined time.

11. A system in accordance with claim 8 wherein said recognition logic means includes means for timing a predetermined time interval, means for triggering said timing means responsive to said count reaching a predetermined value, and means for generating an output indicative of a physiological event of interest if during said predetermined time interval following triggering of said timing means the number of bit samples of the state which gave rise to said triggering exceeds a predetermined number.

12. A system in accordance with claim 8 wherein said count deriving means includes means for inverting one of said first and second bit sample sequences, means for counting up or down at a clocked rate depending upon the state of an input indicative of whether counting should be up or down, and means for alternately applying to said input the inverted one of said bit sample sequences and the other of said bit sample sequences.

13. A system in accordance with claim 12 further including means, following the indication of a physiological event of interest, for initializing said second bit sample sequence with a predetermined number of bit samples of alternating states.

14. A system in accordance with claim 8 further including means, following the indication of a physiological event of interest, for initializing said second bit sample sequence with a predetermined number of bit samples of alternating states.

15. A system for recognizing an event of interest represented in a signal to be monitored comprising means for deriving from said signal a continuous sequence of bit samples, the two states of said bit samples representing changes in opposite directions in said signal, means for deriving a count which is indicative of differences between said bit sample sequence and a delayed version thereof, and recognition logic means responsive to said count for indicating an event of interest.

16. A system in accordance with claim 15 wherein said recognition logic means includes means for timing a predetermined time interval, means for triggering said timing means responsive to said count reaching a first predetermined value, and means for generating an output indicative of an event of interest if within said predetermined time interval following triggering of said timing means said count does not pass a second, different predetermined value.

17. A system in accordance with claim 15 wherein said recognition logic means includes means for timing a predetermined time interval, means for triggering said timing means responsive to said count reaching a predetermined value, and means for generating an output indicative of an event of interest if during said predetermined time interval following triggering of said timing means said count is at or above a predetermined value for a total predetermined time.

18. A system in accordance with claim 15 wherein said recognition logic means includes means for timing a predetermined time interval, means for triggering said timing means responsive to said count reaching a predetermined value, and means for generating an output indicative of an event of interest if during said predetermined time interval following triggering of said timing means the number of bit samples of the state which gave rise to said triggering exceeds a predetermined number.

19. A system in accordance with claim 15 wherein said count deriving means includes means for inverting one of said bit sample sequences, means for generating a delayed replica of said bit sample sequence, means for counting up or down at a clocked rate depending upon the state of an input indicative of whether counting should be up or down, and means for alternately applying to said input said inverted one of said bit sample sequences and said delayed replica bit sample sequence.

20. A system in accordance with claim 19 wherein said recognition logic means includes means for timing a predetermined time interval, means for triggering said timing means responsive to said count reaching a first predetermined value, and means for generating an output indicative of an event of interest if within said predetermined time interval following triggering of said triggering means said count does not pass a second, different predetermined value.

21. A system in accordance with claim 19 wherein said recognition logic means includes means for timing a predetermined time interval, means for triggering said timing means responsive to said count reaching a predetermined value, and means for generating an output indicative of an event of interest if during said predetermined time interval following triggering of said timing means said count is at or above a predetermined value for a total predetermined time.

22. A system in accordance with claim 19 wherein said recognition logic means includes means for timing a predetermined time interval, means for triggering said timing means responsive to said count reaching a predetermined value, and means for generating an output indicative of an event of interest if during said predetermined time interval following triggering of said timing means the number of bit samples of the state which gave rise to said triggering exceeds a predetermined number.

23. A system in accordance with claim 19 further including means, following the indication of an event of interest, for initializing said delayed replica bit sample sequence with a predetermined number of bit samples of alternating states.

24. A system in accordance with claim 15 further including means, following the indication of an event of of interest, for initializing said delayed version of said bit sample sequence with a predetermined number of bit samples of alternating states.

25. An implantable system for recognizing a cardiac event of interest by operating on a sensed cardiac signal comprising means for deriving from said sensed signal a first continuous sequence of bit samples, the two states of said bit samples representing changes in opposite directions in the sensed signal and bit samples of alternating opposite states representing a non-changing sensed signal, means for generating a second continuous sequence of bit samples which is the same as said first sequence but delayed in time, means for deriving a count which is indicative of on-going differences between said first and second bit sample sequences, and recognition logic means responsive to said count for indicating a cardiac event of interest.

26. An implantable system in accordance with claim 25 wherein said recognition logic means includes means for timing a predetermined time interval, means for triggering said timing means responsive to said count reaching a first predetermined value, and means for generating an output indicative of a cardiac event of interest if within said predetermined time interval following triggering of said timing means said count does not fall below a second, lower predetermined value.

27. An implantable system in accordance with claim 25 wherein said recognition logic means includes means for timing a predetermined time interval, means for triggering said timing means responsive to said count reaching a predetermined value, and means for generating an output indicative of a cardiac event of interest if during said predetermined time interval following triggering of said timing means said count is at or above said predetermined value for a total time which is at least a predetermined fraction of said time interval.

28. An implantable system in accordance with claim 25 wherein said recognition logic means includes means for timing a predetermined time interval, means for triggering said timing means responsive to said count reaching a predetermined value, and means for generating an output indicative of a cardiac event of interest if during said predetermined time interval following triggering of said timing means the ratio of the number of bit samples of the state which gave rise to said triggering to the number of bit samples of the opposite state exceeds a predetermined value.

29. An implantable system in accordance with claim 25 wherein said count deriving means includes means for inverting one of said first and second bit sample sequences, means for counting up or down at a clocked rate depending upon the state of an input indicative of whether counting should be up or down, and means for alternately applying to said input the inverted one of said bit sample sequences and the other of said bit sample sequences.

30. An implantable system in accordance with claim 29 further including means, following the indication of a cardiac event of interest, for initializing said second bit sample sequence with a predetermined number of bit samples of alternating states.

31. An implantable system in accordance with claim 25 further including means, following the indication of a cardiac event of interest, for initializing said second bit sample sequence with a predetermined bit sample sequence.

* * * * *